(12) United States Patent
Brodnick

(10) Patent No.: US 6,636,761 B2
(45) Date of Patent: Oct. 21, 2003

(54) METHOD AND APPARATUS FOR GENERATING A TWELVE-LEAD ECG FROM FEWER THAN TEN ELECTRODES

(75) Inventor: Donald Eugene Brodnick, Cedarburg, WI (US)

(73) Assignee: GE Medical Systems Information Technologies, Inc., Milwaukee, WI (US)

(*) Notice: Subject to any disclaimer, the term of this patent is extended or adjusted under 35 U.S.C. 154(b) by 329 days.

(21) Appl. No.: 09/752,140

(22) Filed: Dec. 29, 2000

(65) Prior Publication Data

US 2002/0087088 A1 Jul. 4, 2002

(51) Int. Cl.$^7$ ............................................. A61B 5/0402
(52) U.S. Cl. ........................ 600/509; 600/382; 600/515
(58) Field of Search ................................. 600/382, 508, 600/509, 512, 515, 522, 523; 455/418, 419

(56) References Cited

U.S. PATENT DOCUMENTS

| 4,850,370 | A |   | 7/1989  | Dower   |           |
|-----------|---|---|---------|---------|-----------|
| 5,058,598 | A | * | 10/1991 | Nicklas et al. | 600/512 |
| 5,711,304 | A |   | 1/1998  | Dower   |           |
| 5,794,624 | A | * | 8/1998  | Kwong   | 600/515   |
| 5,913,828 | A | * | 6/1999  | Russell | 600/509   |
| 6,006,125 | A | * | 12/1999 | Kelly et al. | 600/382 |
| 6,167,258 | A | * | 12/2000 | Schmidt et al. | 455/419 |
| 6,505,067 | B1 | * | 1/2003 | Lee et al. | 600/509 |
| 2002/0035334 | A1 |  | 3/2002 | Meij et al. |     |
| 2002/0045837 | A1 |  | 4/2002 | Wei et al.  |     |

FOREIGN PATENT DOCUMENTS

JP          2002-34943       4/2002

* cited by examiner

*Primary Examiner*—Willis R. Wolfe
(74) *Attorney, Agent, or Firm*—Michael Best & Friedrich LLP

(57) ABSTRACT

A method and apparatus for acquiring and processing electrical signals produced by a patient's heart. The apparatus includes fewer than ten electrodes for attachment to the patient. Each electrode is attached in a respective one of the standard ten-electrode, twelve-lead ECG positions. The device includes a signal processor connected to the electrodes for acquiring electrical signals from the electrodes and generating a twelve-lead ECG from the electrical signals. The signal processor generates less than twelve of the leads mathematically.

For the method of the invention, a plurality of less than ten electrodes are attached to the patient. Each electrode is attached in a respective one of the standard ten-electrode, twelve-lead ECG positions. Electrical signals are acquired from the electrodes and a twelve-lead ECG is generated from the acquired electrical signals. Not all twelve leads are generated mathematically.

120 Claims, 3 Drawing Sheets

METHOD AND APPARATUS FOR GENERATING A TWELVE-LEAD ECG FROM FEWER THAN TEN ELECTRODES

BACKGROUND OF THE INVENTION

The invention relates to a method and apparatus for generating a twelve-lead electrocardiogram (ECG) from a plurality of fewer than ten electrodes for attachment to a patient in the standard ten-electrode, twelve-lead ECG positions.

A standard, resting ECG is acquired with ten electrodes. Four of the ten electrodes are placed on the patient's limbs. Six of the ten electrodes are attached to the patient's chest over the heart. The signals acquired by the ten electrodes are amplified and processed to generate twelve channels of ECG data. The twelve channels or leads are generally split into two groups—the frontal plane leads (I, II, III, aVR, aVL, aVF) and the horizontal plane leads (V1, V2, V3, V4, V5, V6).

A standard, resting ECG has several limitations. First, the six electrodes attached to the patient's chest inhibit the clinicians access to the patient's chest. Second, clinicians may not be able to attach all six chest electrodes due to wounds or bandages on the patient's chest. The electrodes, leadwires, and amplifiers necessary to acquire twelve channels of ECG data increase the cost of the ECG machine. Fourth, the amount of data representing twelve channels of ECG generally exceeds the maximum amount or bandwidth that typical telemetry units are able to transmit.

U.S. Pat. No. 4,850,370 provides a solution to some of the above-described limitations. The '370 Patent discloses a method of sensing and analyzing the electrical activity of the human heart by sensing the voltage signals generated by the heart between four electrodes located at key positions on the surface of the subject's body. A signal processing means produces electrocardiographic signals corresponding to the lead signals of a twelve-lead electrocardiogram.

FIG. 3 illustrates the electrode placement for the method of generating a twelve-lead ECG from four electrodes as disclosed in the '370 Patent. The four electrodes are designated as E, A, S, and I (hereinafter referred to collectively as the "EASI electrodes"). The E electrode is located at the front midline over the lower end of the sternum. The A electrode is located at the left mid-axillary line. The S electrode is located at the front midline over the upper end of the sternum. The I electrode is located at the right mid-axillary line.

The EASI electrodes are coupled to a signal processor (not shown) having a first stage and a second stage. The first stage of the signal processor does not generate the twelve-lead ECG, but rather generates xyz vectorcardiographic signals. The twelve-lead ECG is then derived from the xyz vectorcardiographic signals in the second stage of the signal processor. As a result of the two stage signal processing, each of the twelve leads generated from the EASI electrodes are mathematically generated. In other words, none of the leads are the same as the leads that would be generated from the electrical signals of a standard ten-electrode, twelve-lead ECG.

The method of the '370 Patent has several limitations. First, the four electrodes are placed in non-standard positions, i.e. positions different from the electrode positions for a standard ten-electrode, twelve-lead ECG. This requires clinicians to be trained specifically for the method of the '370 Patent. Second, twelve leads of ECG data are generated, but all twelve leads are generated mathematically. None of the twelve leads in the method of the '370 Patent are the same as the leads that would be generated from a standard ten-electrode, twelve-lead ECG. Rather, all twelve leads are mere approximations of the leads of a standard ten-electrode, twelve-lead ECG. Third, two of the four electrodes are placed directly over the sternum. The sternum is cracked for all open chest surgeries in a procedure called sternotomy. Thus, the clinician may not be able to attach the two electrodes directly over the sternum due to sternotomy wounds and bandages.

SUMMARY OF THE INVENTION

In light of the limitations described above, a need exists for a method and apparatus for generating a twelve-lead ECG from less than ten electrodes for attachment to a patient in the standard ten-electrode, twelve-lead ECG positions.

Accordingly, the invention provides a method and apparatus for generating a twelve-lead ECG from fewer than ten electrodes for attachment to a patient in at least some of the standard ten-electrode, twelve-lead ECG positions.

The apparatus is a device for acquiring and processing electrical signals produced by a patient's heart. The device includes fewer than ten electrodes for attachment to the patient. Each electrode is attached in a respective one of the standard ten-electrode, twelve-lead ECG positions. The device includes a signal processor connected to the electrodes. The signal processor acquires electrical signals from the electrodes and generates a twelve-lead ECG from the electrical signals. The signal processor generates less than twelve of the leads mathematically.

For the method of the invention, a plurality of less than ten electrodes are attached to the patient. Each electrode is attached in a respective one of the standard ten-electrode, twelve-lead ECG positions. Electrical signals are acquired from the electrodes and a twelve-lead ECG is generated from the acquired electrical signals. But not all twelve leads are generated mathematically.

The device employs multiple-linear regression using expansion-coefficient equations to mathematically generate fewer than twelve of the leads. The expansion-coefficient equations are determined either from ECGs from a hospital's general population, from a sub-population of the hospital's general population, or from ECGs previously acquired from the patient. The invention employs multiple-linear regression to generate the leads that are missing due to the use of fewer than ten electrodes. Stated differently, some of the leads (for the twelve lead ECG) are generated from a standard electrical manipulation of the signals acquired from the electrodes, while the remaining leads are generated mathematically by a signal processor.

The invention further includes a telemetry unit to acquire electrical signals from the plurality of less than ten electrodes and to transmit the electrical signals to the signal processor to generate a twelve-lead ECG.

It is an advantage of the invention to reduce the number of electrodes, leadwires, and amplifiers necessary to acquire a twelve-lead ECG while still employing some of the standard electrode positions commonly known to clinicians.

It is another advantage of the invention to provide a method of generating a twelve-lead ECG without generating all twelve leads mathematically.

It is still another advantage of the invention to provide a method of electrode placement that allows for better access by clinicians to the patient's chest.

It is still another advantage of the invention to provide a method of electrode attachment that avoids electrode placement over the sternum in order to avoid sternotomy wounds and bandages.

It is still another advantage of the invention to reduce the bandwidth required to transmit the acquired electrical signals representing the patient's ECG from a telemetry unit to a signal processor.

It is still another advantage of the invention to provide a telemetry system capable of monitoring the ECG of more than one patient.

Various other features and advantage of the invention are set forth in the following drawings, detailed description and claims.

DETAILED DESCRIPTION OF THE INVENTION

Before one embodiment of the invention is explained in full detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including" and "comprising" and variations thereof herein is meant to encompass the items listed thereafter and equivalents thereof as well as additional items.

Figure 2:
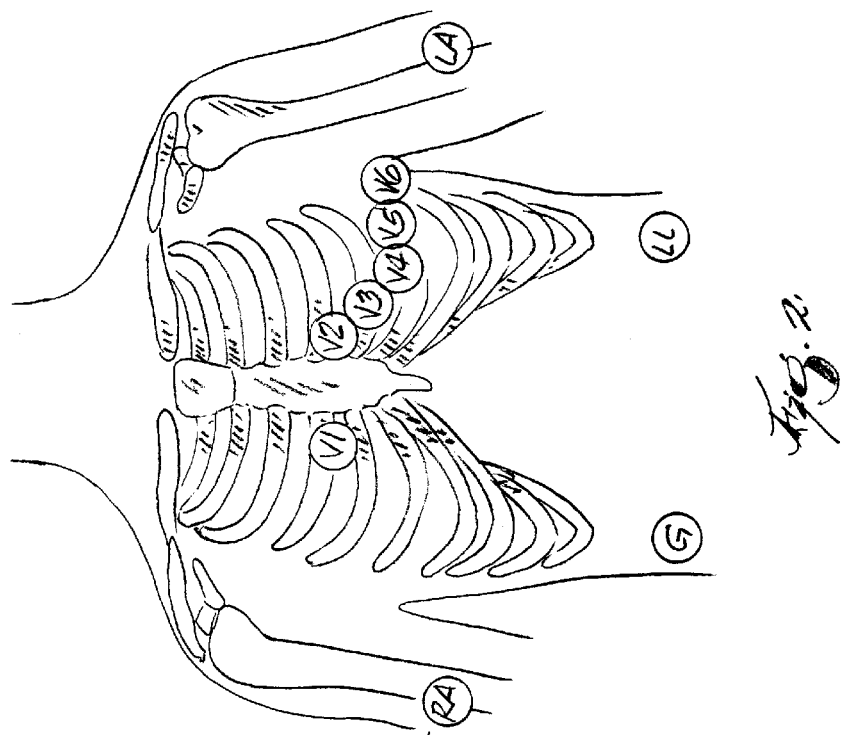
FIG. 2 illustrates the electrode placement for a standard or resting ten-electrode, twelve-lead ECG.

FIG. 2 illustrates the electrode placement for a standard or resting ten-electrode, twelve-lead ECG (hereinafter "standard ECG"). For a standard ECG, ten electrodes are attached to a patient's body. One electrode is attached to each of the patient's four limbs at the wrists and ankles. These electrodes are referred to as left arm (LA), right arm (RA), left leg (LL), and right leg (RL). The RL electrode generally serves as an electrical ground. In practice, the limb electrodes are attached at any point along the limb from the wrist or ankle towards the point of attachment of the limb to the trunk of the body. As shown in FIG. 2, six electrodes are attached in standard positions on the chest around the heart. As is commonly known in the art, the ten electrodes are connected via leadwires and resistor networks to enough amplifiers to record twelve separate ECG channels or leads.

The twelve leads are split into two groups: the frontal plane and the horizontal plane. If a straight line were drawn from the heart to each wrist and each ankle, the four lines would lie in the frontal plane. Similarly, if a straight line were drawn from the heart to each of the six electrodes placed on the patient's chest, the six lines would generally lie in the horizontal plane. The leads in the frontal plane are referred to as the frontal leads, the limb leads, or the Einthoven leads, and include leads 1, II, III, aVR, aVL, and aVF. The leads in the horizontal plane are referred to as the horizontal leads, the precordial leads, the chest leads, or the unipolar leads, and include leads V1, V2, V3, V4, V5, and V6.

The frontal leads are obtained with various permutations of the LA, RA, and LL electrodes, with the RL electrode serving as an electrical ground. The frontal leads are comprised of the potential between two of the limb electrodes: lead I corresponds to the potential between LA and RA, lead II corresponds to the potential between LL and RA, and lead III corresponds to the potential between LL and LA.

Leads aVR, aVL, and aVF, referred to as the augmented leads, are comprised of the potential between one electrode and a reference input, the reference input being the average of two electrodes. For example, lead aVF is the signal between LL and a reference input, where the reference input is the average of the potentials at electrodes RA and LA.

The horizontal leads are obtained with various permutations of the six electrodes attached to the patient's chest, in addition to three of the four limb electrodes. Each of the six horizontal leads is comprised of the signal between the potential at the particular electrode placed on the patient's chest and the potential at Wilson's central terminal. Wilson's central terminal refers to the average potential between the RA, LA, and LL electrodes. For example, lead V1 is the signal between electrode V1 and Wilson's central terminal.

Cardiologists are trained to recognize the subtle characteristics of ECG waveforms and to correlate the subtle characteristics to specific cardiovascular events and conditions. In general, any ECG machine that does not generate the standard twelve-lead ECG is undesirable, because cardiologists depend on consistency for their interpretation of ECG waveforms. Accordingly, the preferred embodiments of the present invention provide a method and apparatus for generating a standard twelve-lead ECG from fewer than the ten electrodes.

The method and apparatus of the present invention generates a plurality of leads that are the same as the leads that would be generated from the electrical signals of a standard ECG. Before the preferred embodiments of the invention are described, it should be understood that the essence of the invention includes the use of any number of electrodes and any configuration of electrode placement, as long as fewer than ten electrodes are each attached to the patient in a respective one of the standard ECG positions, and a twelve-lead ECG is derived therefrom.

Figure 4:
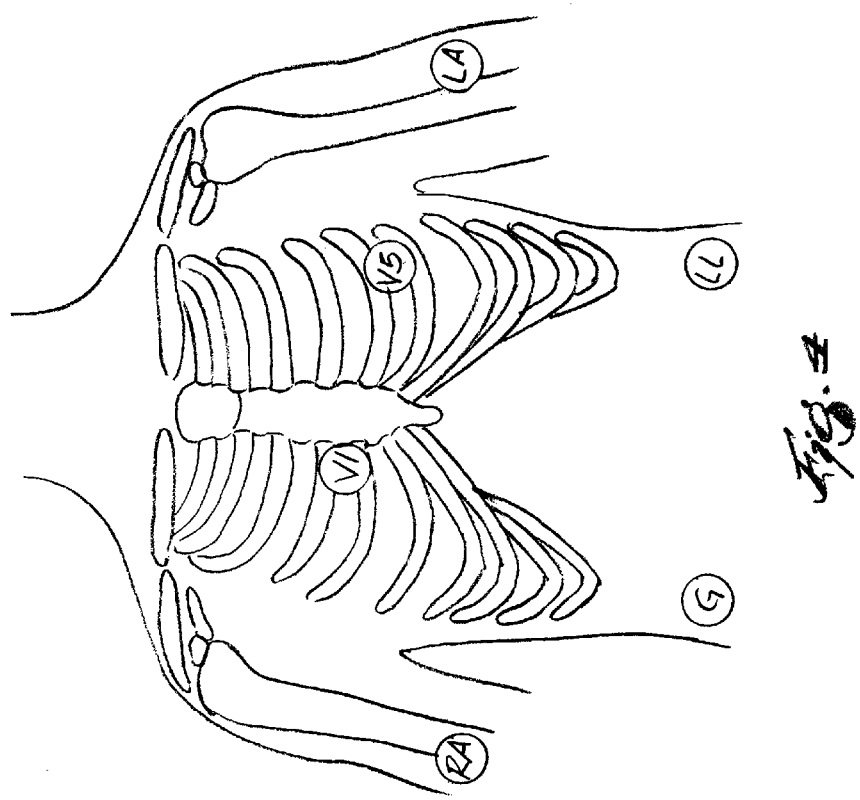
FIG. 4 illustrates the electrode placement for the most preferred embodiment of the invention.

The most preferred electrode placement is illustrated in FIG. 4. Specifically, FIG. 4 illustrates the electrode placement for six electrodes used to acquire electrical signals from the patient's heart. Preferably, only two electrodes are attached to the patient's chest. V1 is attached to the patient in approximately the fourth intercostal space at the right border of the patient's sternum. V5 is attached to the patient in approximately the fifth intercostal space at the patient's anterior axillary line. Four electrodes are attached to the patient's limbs. The electrodes attached to the right arm, left arm, and left leg acquire electrical signals, while the electrode attached to the right leg generally acts as an electrical ground.

In the most preferred embodiment, electrodes V2, V3, V4, and V6 are not attached to the patient. Thus, leads V2, V3, V4, and V6 corresponding to the omitted electrodes must be derived mathematically. However, unlike the known prior art, only these four leads need to be derived mathematically. Eight of the leads, namely leads I, II, III, aVR, aVL, aVF, V1, and V5, are generated in the same manner as in a standard ten-electrode, twelve-lead ECG.

Electrodes V1 and V5 are the most preferred chest electrodes for a number of reasons. First, the information in the V1 lead is very important to clinicians. Lead V1 is, of course, most accurate if an electrode is placed directly in the V1 position. Second, the positions of the V1 and V5 electrodes do not interfere with the clinician's access to the patient's chest as much as the positions of the V2, V3, and V4 electrodes. Even with the V1 and V5 electrodes in place, the clinician is still able to access the area of the chest closest to the patient's heart. For example, the clinician is able to use imaging probes in the area of the chest closest to the patient's heart. Third, the clinician may not even be able to attach the V2, V3, and V4 electrodes, because the patient may have wounds or bandages from surgical procedures involving the heart in the area of the chest where the V2, V3, and V4 electrodes are normally positioned. Fourth, electrode V1 is placed near the sternum, but not directly on the sternum, avoiding sternotomy wounds and bandages.

Figure 5:
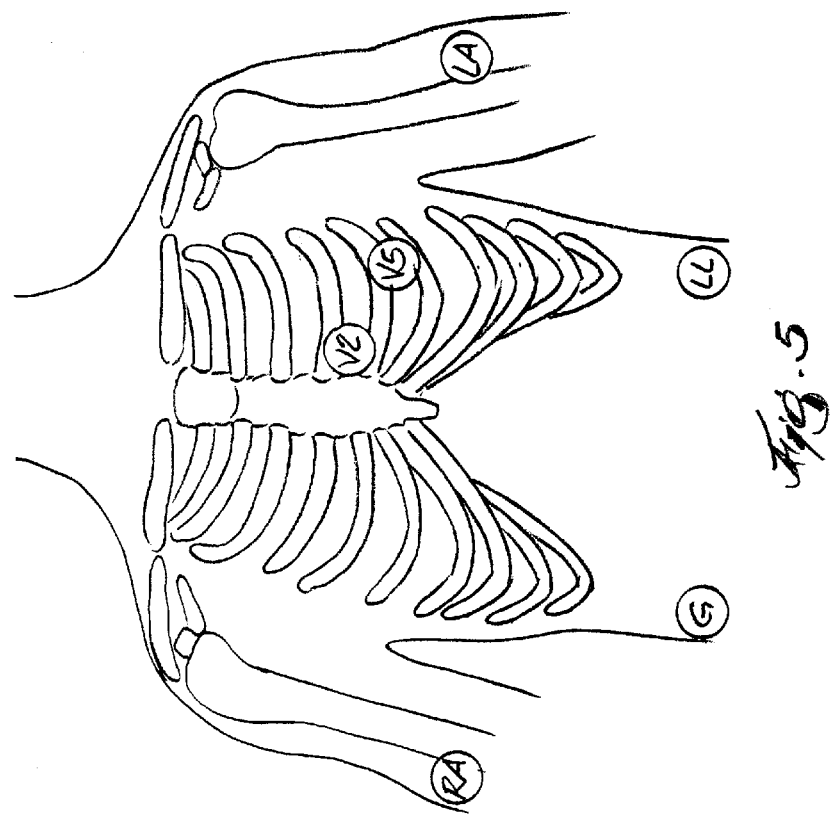
FIG. 5 illustrates the electrode placement for a less preferred embodiment of the invention.

A less preferred embodiment for the electrode placement of the invention is illustrated in FIG. 5. FIG. 5 also illustrates the electrode placement for six electrodes used to acquire electrical signals from the patient's heart. Again, only two electrodes are attached to the patient's chest. V2 is attached to the patient in approximately the fourth intercostal space at the left border of the patient's sternum. V5 is attached to the patient in approximately the fifth intercostal space at the patient's anterior axillary line. Again, four electrodes are attached to the patient's limbs. The electrodes attached to the right arm, left arm, and left leg acquire electrical signals, while the electrode attached to the right leg generally acts as an electrical ground.

As illustrated in FIG. 5, electrodes V1, V3, V4, and V6 are not attached to the patient. Thus, leads V1, V3, V4, and V6 corresponding to the omitted electrodes must be derived mathematically. Again, only these four leads need to be derived mathematically. Eight of the leads, namely leads I, II, III, aVR, aVL, aVF, V2, and V5, are generated in the same manner as in a standard ten-electrode, twelve-lead ECG. One disadvantage of the less preferred embodiment is that the mathematically derived V1 lead is not as accurate as the V1 lead generated from the use of the V1 electrode. Since the V1 lead is considered important to clinicians, the embodiment using the V2 and V5 electrodes is less desirable, even though the embodiment produces generally acceptable results.

In both preferred embodiments, the four missing leads are generated using a mathematical method called multiple-linear regression. Multiple-linear regression is a technique used to compute a prediction of a given data set from associated members of other data sets. In the present invention, these "other" data sets are either ECGs from a hospital's general population, from a sub-population of the hospital's general population, or from ECGs previously acquired from the patient. Preferably, the sub-populations of the hospital's general population are based on one or several parameters, such as sex, race, age, weight, height, or body habitus. Body habitus refers to a combination of body build, height, and weight. In general, the four missing leads are calculated based on the relationship between the available leads and a data set of previously acquired ECGs.

Preferably, an algorithm uses the multiple-linear regression technique to generate the four missing leads. The input into the algorithm is a data set of previously acquired ECGs. Preferably, the data set consists of previously acquired ECGs from a hospital's general population or from a sub-population of the hospital's general population. Most preferably, the data set consists of previously acquired ECGs from the particular patient.

Preferably, the data set consists of previously acquired ECGs that have been sampled at a rate of between 120 and 1000 times per second. Thus, the data set consists of twelve columns, corresponding to each of the twelve leads, with hundreds of thousands of rows of samples, corresponding to the voltage values for each of the twelve leads. The algorithm performs multiple-linear regression between the columns of lead data. Specifically, the algorithm performs multiple-linear regression between the columns of lead data corresponding to the electrodes that will be attached to the patient and between the columns of lead data corresponding to an electrode that will not be attached to the patient. The algorithm creates an equation from the previously-acquired ECG data defining the leads that will be missing, due to the omitted electrodes, as a function of the leads that will be available.

For example, in the most preferred embodiment, the algorithm creates a first equation to determine the value of lead V2 based on the values of leads V1, V5, I, and II. The inputs to the algorithm are five columns of data corresponding to the previously-acquired ECG voltage values for leads V1, V2, V5, I, and II. The columns of data corresponding to leads V1, V5, I, and II are compared to the column of data corresponding to lead V2. The algorithm generates an equation relating the data in the V1, V5, I, and II lead columns to the data in the V2 lead column by minimizing the sum squared error between the five columns of data. The generated equation is in the following form:

$$y = \beta_1 x_1 + \beta_2 x_2 + \beta_3 x_3 + \beta_4 x_4 \quad [1]$$

where the $\beta_1$, $\beta_2$, $\beta_3$, and $\beta_4$ are the expansion coefficients for the equation. An example of an expansion-coefficient equation for lead V2 is as follows:

$$V2 = 1.58 * V1 + 0.23 * V5 - 0.09 * II + 0.89 * I \quad [2]$$

where $y = V2$, $\beta_1 = 1.58$, $x_1 = V1$, $\beta_2 = 0.23$, $x_2 = V5$, $\beta = 0.09$, $x_3 = II$, $\beta_4 = 0.89$, and $x_4 = I$.

In the same manner, an expansion-coefficient equation is derived for each of the leads corresponding to the omitted electrodes. In the most preferred embodiment, a separate equation is derived for each of leads V2, V3, V4, and V6. Thus, the columns of data corresponding to leads V1, V5, I, and II are compared to the column of data corresponding to lead V3 to generate an expansion-coefficient equation for lead V3. Similarly, the columns of data corresponding to leads V1, V5, I, and II are compared to the column of data corresponding to lead V4 to generate an expansion-coefficient equation for lead V4. Finally, the columns of data corresponding to leads V1, V5, I, and II are compared to the column of data corresponding to lead V6 to generate an expansion-coefficient equation for lead V6.

In the most preferred embodiment, once the expansion-coefficient equations are derived, the patient's ECG is acquired with only chest electrodes V1 and V5 and the four limb electrodes. From these six electrodes, eight leads are generated in the same manner as for a standard ECG. Four of the twelve leads, however, must be determined using the expansion-coefficient equations previously derived. Accordingly, the expansion-coefficient equations are used to derive the voltage values for the four missing leads for each individual sample. For example, the expansion-coefficient equation for lead V2 is used to derive the voltage value of lead V2 for each individual sample. In the most preferred embodiment, the voltage values for each sample of leads V3, V4, and V6 are derived in the same manner. With the addition of the data for the four derived leads, the data set comprises a complete twelve-lead ECG.

Figure 1:
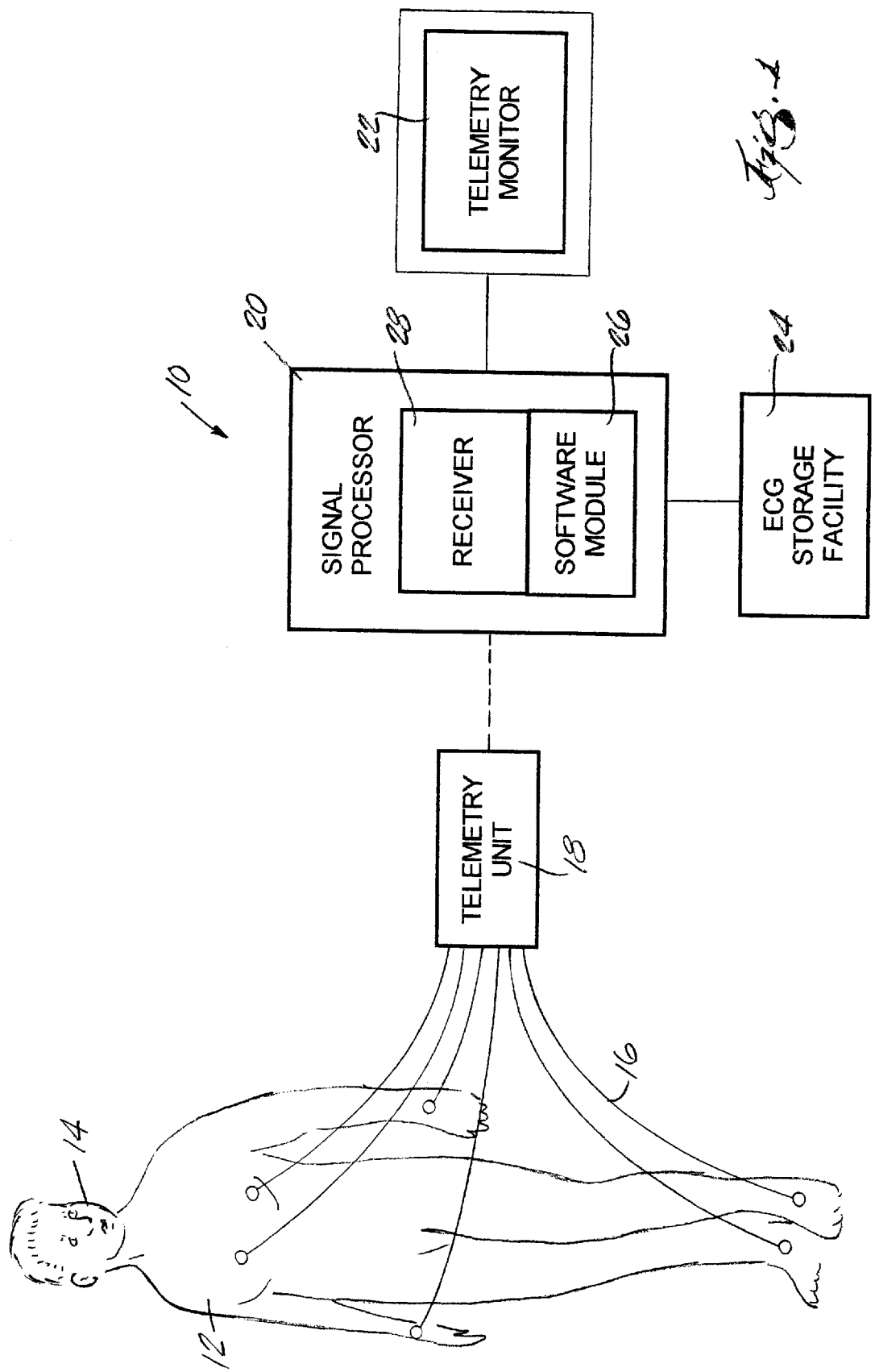
FIG. 1 illustrates the apparatus embodying the invention.
Figure 3:
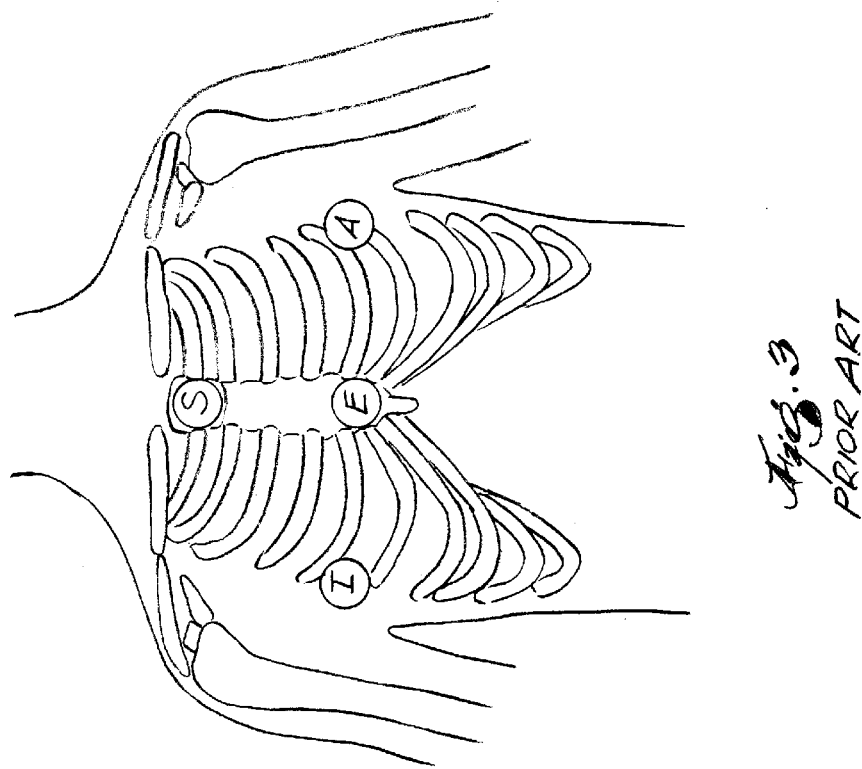
FIG. 3 illustrates the electrode placement for the method of the '370 Patent.

FIG. 1 illustrates the apparatus 10 embodying the invention. In the preferred embodiment, the apparatus 10 is a patient monitoring or patient data acquisition device. While any device for acquiring ECG signals (such as, for example, a bedside monitor, transport monitor, or Holter monitor) is contemplated by the invention, the apparatus of the preferred embodiment employs a telemetry-based monitoring device. The apparatus 10 includes six electrodes 12 attachable to a patient 14, leadwires 16 coupled to the electrodes 12, a telemetry unit 18 coupled to the electrodes 12 by leadwires 16, a signal processor 20 wirelessly coupled to the telemetry unit 18, a telemetry monitor 22 coupled to the signal processor 20, and an ECG storage facility 24 coupled to the signal processor 20.

Before the telemetry system embodied in the apparatus 10 of FIG. 1 is described, it should be understood that the invention could also be implemented in a bed-side monitor. For the bed-side monitor, the electrodes 12 would be coupled directly to the signal processor 20 by leadwires 16 in a conventional manner. Conversely, FIG. 1 illustrates the apparatus 10 including a telemetry unit 18 wirelessly coupled to the signal processor 20 and telemetry monitor 22. Conventional methods of wireless transmission are used to transmit the electrical signals from the telemetry unit 18 to the receiver 28 in the signal processor 20.

Biopotential signals are often processed by telemetry, a technique that provides a wireless link between the patient and the signal processing components. Thus, clinicians can monitor a patient while the patient has full mobility. Traditional methods of telemetry utilize from three to five electrodes, but are unable to acquire a twelve-lead ECG from these three to five electrodes. The limiting factor in telemetry is the bandwidth of the signal being transmitted to the signal processing components. Accordingly, traditional telemetry monitors are unable to support the bandwidth necessary to transmit the electrical signals representing an entire twelve-lead ECG.

In the preferred embodiments of the present invention, four, rather than eight or more, channels of ECG data are transmitted from the telemetry unit 18 to the signal processor 20. As a result, the bandwidth necessary to transmit the electrical signals representing the patient's ECG is reduced by at least half. Due to the reduced number of electrodes and the reduced bandwidth, the telemetry unit 18 is capable of monitoring the electrical activity of the patient's heart while the patient has full mobility. Moreover, the apparatus 10 is capable of acquiring more data from each particular patient or data from more than one patient.

Referring to FIGS. 1 and 4, according to the method of the most preferred embodiment of the invention, six electrodes 12 are attached to the patient. A first electrode (V1) is attached in approximately the fourth intercostal space at the right border of the patient's sternum. A second electrode (V5) is attached in approximately the fifth intercostal space at the patient's anterior axillary line. Four additional electrodes (LA, RA, LL, and G) are attached to the patient's limbs. Electrical signals are acquired from the six electrodes 12 and transmitted via leadwires 16 to the telemetry unit 18. The electrical signals are amplified and transmitted to the receiver 28 of the signal processor 20.

In both preferred embodiments, reducing the number of electrodes 12 attached to the patient reduces the number of leadwires 16 and amplifiers (not shown) within the telemetry unit 18 necessary to acquire the electrical signals. Preferably, only six leadwires 16 and four amplifiers within the telemetry unit 18 are necessary for the preferred embodiments of the invention.

A software module 26 within signal processor 20 uses an algorithm to calculate the expansion-coefficient equations for the four missing leads. The input to the algorithm is, most preferably, a data set of the patient's previously acquired ECGs. The data set is preferably stored in a hospital ECG storage facility 24 and accessed by the signal processor 20 of the ECG machine 10.

The apparatus 10 then acquires an ECG for the patient. The telemetry unit 18 transmits the electrical signals from the electrodes 12 to a receiver 28 within the signal processor 20. The four missing leads are calculated by the software module 26 within signal processor 20 using the previously-derived expansion-coefficient equations. All twelve leads, including the four generated leads, are then displayed for the clinician on telemetry monitor 22.

Various features and advantages of the invention are set forth in the following claims.

What is claimed is:

1. A device for acquiring and processing electrical signals produced by a patient's heart, the device comprising:
   a plurality of less than ten electrodes each for attachment to the patient in a one of the standard ten-electrode, twelve-lead electrocardiogram electrode positions; and
   a signal processor connected to the plurality of less than ten electrodes for acquiring electrical signals from the electrodes and for generating a twelve-lead electrocardiogram from the electrical signals;
   wherein the plurality of electrodes includes a one of (a) an electrode for attachment to the patient in approximately the fourth intercostal space at the right border of the patient's sternum and (b) an electrode for attachment to the patient in approximately the fourth intercostal space at the left border of the patient's sternum.

2. A method of acquiring and processing electrical signals produced by a patient's heart, the method comprising the acts of:
   attaching a plurality of less than ten electrodes to the patient, the act of attaching including
      attaching each of the electrodes in a one of the standard ten-electrode, twelve-lead electrocardiogram positions, and
      attaching an electrode in one of (a) approximately the fourth intercostal space at the right border of the patient's sternum and (b) approximately the fourth intercostal space at the left border of the patient's sternum;
   acquiring electrical signals from the electrodes; and
   generating a twelve-lead electrocardiogram from the acquired electrical signals.

3. A device for acquiring and processing electrical signals produced by a patient's heart, the device comprising:
   a plurality of less than ten electrodes for attachment to the patient, at least two of the electrodes attachable to the patient's chest in two of the standard ten-electrode, twelve-lead electrocardiograph positions and at least three of the electrodes attachable to the patient's limbs in three of the standard ten-electrode, twelve-lead electrocardiograph positions; and
   a signal processor connected to the electrodes for acquiring electrical signals from the electrodes and for generating a twelve-lead electrocardiogram from the electrical signals;
   wherein the electrodes attachable to the patient's chest include an electrode attachable in one of (a) approximately the fourth intercostal space at the right border of the patient's sternum and (b) approximately the fourth intercostal space at the left border of the patient's sternum.

4. A method of acquiring and processing electrical signals produced by a patient's heart, the method comprising the acts of:

attaching a plurality of less than ten electrodes to the patient, the act of attaching including
attaching at least two of the electrodes to the patient's chest in two of the standard ten-electrode, twelve-lead electrocardiogram positions and attaching at least three of the electrodes to the patient's limbs in three of the standard ten-electrode twelve-lead electrocardiogram positions, and
attaching an electrode in one of (a) approximately the fourth intercostal space at the right border of the patient's sternum and (b) approximately the fourth intercostal space at the left border of the patient's sternum;
acquiring electrical signals from the electrodes; and
generating a twelve-lead electrocardiogram from the acquired electrical signals.

5. A device for acquiring and processing electrical signals produced by a patient's heart, the device comprising:

a plurality of less than ten electrodes each for attachment to the patient in a one of the standard ten-electrode, twelve-lead electrocardiogram electrode positions; and
a signal processor connected to the plurality of less than ten electrodes for acquiring electrical signals from the electrodes and for generating a twelve-lead electrocardiogram from the electrical signals;
wherein the plurality of electrodes includes an electrode for attachment to the patient in approximately the fourth intercostal space at the right border of the patient's sternum and an electrode for attachment to the patient in approximately the fifth intercostal space at the patient's anterior axillary line.

6. A method of acquiring and processing electrical signals produced by a patient's heart, the method comprising the acts of:

attaching a plurality of less than ten electrodes to the patient, the act of attaching including
attaching each of the electrodes in a one of the standard ten-electrode, twelve-lead electrocardiogram positions, and
attaching an electrode in approximately the fourth intercostal space at the right border of the patient's sternum and in approximately the fifth intercostal space at the patient's anterior axillary line;
acquiring electrical signals from the electrodes; and
generating a twelve-lead electrocardiogram from the acquired electrical signals.

7. A device for acquiring and processing electrical signals produced by a patient's heart, the device comprising:

a plurality of less than ten electrodes each for attachment to the patient in a one of the standard ten-electrode, twelve-lead electrocardiogram electrode positions; and
a signal processor connected to the plurality of less than ten electrodes for acquiring electrical signals from the electrodes and for generating a partially-synthesized twelve-lead electrocardiogram from the electrical signals without acquiring an actual twelve-lead electrocardiogram with ten electrodes before generating the partially-synthesized twelve-lead electrocardiogram.

8. A method of acquiring and processing electrical signals produced by a patient's heart, the method comprising the acts of:

attaching a plurality of less than ten electrodes to the patient, the act of attaching including attaching each of the electrodes in a one of the standard ten-electrode, twelve-lead electrocardiogram positions;
acquiring electrical signals from the electrodes; and
generating a partially-synthesized twelve-lead electrocardiogram from the acquired electrical signals without acquiring an actual twelve-lead electrocardiogram with ten electrodes before generating the partially-synthesized twelve-lead electrocardiogram.

9. A device for acquiring and processing electrical signals produced by a patient's heart, the device comprising:

a plurality of less than ten electrodes each for attachment to the patient in a one of the standard ten-electrode, twelve-lead electrocardiogram electrode positions;
a signal processor connected to the plurality of less than ten electrodes for acquiring electrical signals from the electrodes and for generating a twelve-lead electrocardiogram from the electrical signals, the generated twelve-lead electrocardiogram including leads I, II, III, aVR, aVL, aVF, V1, V2, V3, V4, V5, and V6; and
a software module in the signal processor for mathematically generating leads V1 or V2, V3, V4, and V6 from the electrical signals, the software module generating the leads mathematically from the electrical signals acquired by the signal processor using multiple-linear regression, the software module using expansion coefficients in the multiple-linear regression.

10. A method of acquiring and processing electrical signals produced by a patient's heart, the method comprising the acts of:

attaching a plurality of less than ten electrodes to the patient, the act of attaching including attaching each of the electrodes in a one of the standard ten-electrode, twelve-lead electrocardiogram positions;
acquiring electrical signals from the electrodes;
generating a twelve-lead electrocardiogram from the electrical signals, the twelve-lead electrocardiogram including leads I, II, III, aVR, aVL, aVF, V1, V2, V3, V4, V5, and V6; and
mathematically generating leads V1 or V2, V3, V4, and V6 from the electrical signals using multiple-linear regression and using expansion coefficients in the multiple-linear regression.

11. A device for acquiring and processing electrical signals produced by a patient's heart, the device comprising:

a plurality of less than ten electrodes for attachment to the patient, at least two of the electrodes attachable to the patient's chest in two of the standard ten-electrode, twelve-lead electrocardiograph positions and at least three of the electrodes attachable to the patient's limbs in three of the standard ten-electrode, twelve-lead electrocardiograph positions;
a signal processor connected to the electrodes for acquiring electrical signals from the electrodes and for generating a twelve-lead electrocardiogram from the electrical signals, the generated twelve-lead electrocardiogram including leads I, II, III, aVR, aVL, aVF, V1, V2, V3, V4, V5, and V6; and
a software module in the signal processor for mathematically generating leads V1 or V2, V3, V4, and V6 from the electrical signals using multiple-linear regression and using expansion coefficients in the multiple-linear regression.

12. A method of acquiring and processing electrical signals produced by a patient's heart, the method comprising the acts of:

attaching a plurality of less than ten electrodes to the patient, the act of attaching including
attaching at least two of the electrodes to the patient's chest in two of the standard ten-electrode, twelve-lead electrocardiogram positions, and
attaching at least three of the electrodes to the patient's limbs in three of the standard ten-electrode twelve-lead electrocardiogram positions;
acquiring electrical signals from the electrodes;
generating a twelve-lead electrocardiogram from the electrical signals, the twelve-lead electrocardiogram including leads I, II, III, aVR, aVL, aVF, V1, V2, V3, V4, V5, and V6; and
mathematically generating leads V1 or V2, V3, V4, and V6 from the electrical signals using multiple-linear regression and using expansion coefficients in the multiple-linear regression.

13. A device for acquiring and processing electrical signals produced by a patient's heart, the device comprising:
a plurality of less than ten electrodes each for attachment to the patient in a one of the standard ten-electrode, twelve-lead electrocardiogram electrode positions; and
a signal processor connected to the plurality of less than ten electrodes for acquiring electrical signals from the electrodes and for generating a at least one twelve-lead electrocardiogram from the electrical signals in a time period of approximately 200 milliseconds as the electrical signals are acquired using population-based equations.

14. The device of claim 13 wherein the plurality of electrodes includes a one of (a) an electrode for attachment to the patient in approximately the fourth intercostal space at the right border of the patient's sternum and (b) an electrode for attachment to the patient in approximately the fourth intercostal space at the left border of the patient's sternum.

15. The device of claim 13 wherein the plurality of electrodes includes an electrode attachable in approximately the fifth intercostal space at the patient's anterior axillary line.

16. The device of claim 13 wherein the plurality of electrodes includes an electrode attachable to the patient's left arm.

17. The device of claim 13 wherein the plurality of electrodes includes an electrode attachable to the patient's right arm.

18. The device of claim 13 wherein the plurality of electrodes includes an electrode attachable to the patient's left leg.

19. The device of claim 13 wherein the plurality of electrodes includes an electrode attachable to a grounding point on the patient's body.

20. The device of claim 13 wherein the signal processor generates a twelve-lead electrocardiogram in real-time as the electrical signals are acquired.

21. The device of claim 13 and further comprising a telemetry monitor coupled to the electrodes and to the signal processor.

22. The device of claim 21 wherein the device acquires electrical signals from more than one patient.

23. The device of claim 13 wherein the generated twelve-lead electrocardiogram includes leads I, II, III, aVR, aVL, aVF, V1, V2, V3, V4, V5, and V6.

24. The device of claim 23 wherein leads I, II, III, aVR, aVL, aVF, V1 or V2, and V5 generated from the electrical signals are the same as leads I, II, III, aVR, aVL, aVF, V1 or V2, and V5 that would be generated from the electrical signals of a standard ten-electrode, twelve-lead electrocardiogram.

25. The device of claim 23 wherein the signal processor includes a software module for mathematically generating leads V1 or V2, V3, V4, and V6 from the electrical signals.

26. The device of claim 25 wherein the software module generates the leads mathematically from the electrical signals acquired by the signal processor using multiple-linear regression.

27. The device of claim 26 wherein the software module uses expansion coefficients in the multiple-linear regression to generate the leads.

28. The device of claim 27 wherein the expansion coefficients are determined from a data set of electrocardiograms from a general population.

29. The device of claim 27 wherein the expansion coefficients are determined from a sub-population based on at least one of sex, age, race, height, weight, and body habitus.

30. The device of claim 27 wherein the expansion coefficients are determined from a data set of electrocardiograms from the same patient.

31. A method of acquiring and processing electrical signals produced by a patient's heart, the method comprising the acts of:
attaching a plurality of less than ten electrodes to the patient, the act of attaching including attaching each of the electrodes in a one of the standard ten-electrode, twelve-lead electrocardiogram positions;
acquiring electrical signals from the electrodes; and
generating a at least one twelve-lead electrocardiogram from the electrical signals in a time period of approximately 200 milliseconds as the electrical signals are acquired using population-based equations.

32. The method of claim 31 wherein the act of attaching a plurality of electrodes further comprises the act of attaching an electrode in one of (a) approximately the fourth intercostal space at the right border of the patient's sternum and (b) approximately the fourth intercostal space at the left border of the patient's sternum.

33. The method of claim 31 wherein the act of attaching a plurality of electrodes further comprises the act of attaching an electrode in approximately the fifth intercostal space at the patient's anterior axillary line.

34. The method of claim 31 wherein the act of attaching a plurality of electrodes further comprises the act of attaching an electrode to the patient's left arm.

35. The method of claim 31 wherein the act of attaching a plurality of electrodes further comprises the act of attaching an electrode to the patient's right arm.

36. The method of claim 31 wherein the act of attaching a plurality of electrodes further comprises the act of attaching an electrode to the patient's left leg.

37. The method of claim 31 wherein the act of attaching a plurality of electrodes further comprises the act of attaching an electrode to a grounding point on the patient's body.

38. The method of claim 31 wherein the act of generating a twelve-lead electrocardiogram includes generating a twelve-lead electrocardiogram in real-time as the electrical signals are acquired.

39. The method of claim 31 wherein the act of acquiring the electrical signals further comprises the act of acquiring the electrical signals with a signal processor coupled to a telemetry monitor.

40. The method of claim 39 wherein the act of acquiring the electrical signals from the electrodes further comprises the act of acquiring electrical signals from the electrodes of more than one patient.

41. The method of claim 31 wherein the act of generating a twelve-lead electrocardiogram further comprises the act of generating leads I, II, III, aVR, aVL, aVF, V1, V2, V3, V4, V5, and V6.

42. The method of claim 41 wherein leads I, II, III, aVR, aVL, aVF, V1 or V2, and V5 that would be generated from the electrical signals are the same as leads I, II, III, aVR, aVL, aVF, V1 or V2, and V5 generated from the electrical signals of a standard ten-electrode, twelve-lead electrocardiogram.

43. The method of claim 41 wherein the act of generating a twelve-lead electrocardiogram further comprises the act of mathematically generating leads V1 or V2, V3, V4, and V6 from the electrical signals.

44. The method of claim 43 wherein the act of generating the leads further comprises the act of generating the leads using multiple-linear regression.

45. The method of claim 44 wherein the act of generating the leads further comprises the act of using expansion coefficients in the multiple-linear regression.

46. The method of claim 45 wherein the act of generating the leads further comprises the act of determining the expansion coefficients from a data set of electrocardiograms from a general population.

47. The method of claim 45 wherein the act of generating the leads further comprises the act of determining the expansion coefficients from a data set of electrocardiograms from a sub-population based on at least one of sex, age, race, height, weight, and body habitus.

48. The method of claim 45 wherein the act of generating the leads further comprises the act of determining the expansion coefficients from a data set of electrocardiograms from the same patient.

49. A device for acquiring and processing electrical signals produced by a patient's heart, the device comprising:
a plurality of less than ten electrodes for attachment to the patient, at least two of the electrodes attachable to the patient's chest in two of the standard ten-electrode, twelve-lead electrocardiograph positions and at least three of the electrodes attachable to the patient's limbs in three of the standard ten-electrode, twelve-lead electrocardiograph positions; and
a signal processor connected to the electrodes for acquiring electrical signals from the electrodes and for generating a at least one twelve-lead electrocardiogram from the electrical signals in a time period of approximately 200 milliseconds as the electrical signals are acquired using population-based equations.

50. The device of claim 49 wherein the electrodes attachable to the patient's chest include an electrode attachable in one of (a) approximately the fourth intercostal space at the right border of the patient's sternum and (b) approximately the fourth intercostal space at the left border of the patient's sternum.

51. The device of claim 49 wherein the electrodes attachable to the patient's chest include an electrode attachable in approximately the fifth intercostal space at the patient's anterior axillary line.

52. The device of claim 49 wherein the electrodes attachable to the patient's limbs include an electrode attachable to the patient's left arm.

53. The device of claim 49 wherein the electrodes attachable to the patient's limbs include an electrode attachable to the patient's right arm.

54. The device of claim 49 wherein the electrodes attachable to the patient's limbs include an electrode attachable to the patient's left leg.

55. The device of claim 49 wherein the plurality of electrodes includes an electrode attachable to a grounding point on the patient's body.

56. The device of claim 49 wherein the signal processor generates a twelve-lead electrocardiogram in real-time as the electrical signals are acquired.

57. The device of claim 49 and further comprising a telemetry monitor coupled to the electrodes and to the signal processor.

58. The device of claim 57 wherein the device acquires electrical signals from the electrodes of more than one patient.

59. The device of claim 49 wherein the generated twelve-lead electrocardiogram includes leads I, II, III, aVR, aVL, aVF, V1, V2, V3, V4, V5, and V6.

60. The device of claim 59 wherein leads I, II, III, aVR, aVL, aVF, V1 or V2, and V5 generated from the electrical signals are the same as leads I, II, III, aVR, aVL, aVF, V1 or V2, and V5 that would be generated from the electrical signals of a standard ten-electrode, twelve-lead electrocardiogram.

61. The device of claim 59 wherein the signal processor includes a software module for mathematically generating leads V1 or V2, V3, V4, and V6 from the electrical signals.

62. The device of claim 61 wherein the software module generates the leads mathematically from the electrical signals acquired by the signal processor using multiple-linear regression.

63. The device of claim 62 wherein the software module uses expansion coefficients in the multiple-linear regression to generate the leads.

64. The device of claim 63 wherein the expansion coefficients are determined from a data set of electrocardiograms from a general population.

65. The device of claim 63 wherein the expansion coefficients are determined from a data set of electrocardiograms from a sub-population based on at least one of sex, age, race, height, weight, and body habitus.

66. The device of claim 63 wherein the expansion coefficients are determined from a data set of electrocardiograms from the same patient.

67. A method of acquiring and processing electrical signals produced by a patient's heart, the method comprising the acts of:
attaching a plurality of less than ten electrodes to the patient, the act of attaching including
attaching at least two of the electrodes to the patient's chest in two of the standard ten-electrode, twelve-lead electrocardiogram positions, and
attaching at least three of the electrodes to the patient's limbs in three of the standard ten-electrode twelve-lead electrocardiogram positions;
acquiring electrical signals from the electrodes; and
generating a at least one twelve-lead electrocardiogram from the electrical signals in a time period of approximately 200 milliseconds as the electrical sigznals are acquired using population-based equations.

68. The method of claim 67 wherein the act of attaching electrodes to the patient's chest includes the act of attaching an electrode in one of (a) approximately the fourth intercostal space at the right border of the patient's sternum and (b) approximately the fourth intercostal space at the left border of the patient's sternum.

69. The method of claim 67 wherein the act of attaching electrodes to the patient's chest includes the act of attaching an electrode in approximately the fifth intercostal space at the patient's anterior axillary line.

70. The method of claim 67 wherein the act of attaching electrodes to the patient's limbs includes the act of attaching an electrode to the patient's left arm.

71. The method of claim 67 wherein the act of attaching electrodes to the patient's limbs includes the act of attaching an electrode to the patient's right arm.

72. The method of claim 67 wherein the act of attaching electrodes to the patient's limbs includes the act of attaching an electrode to the patient's left leg.

73. The method of claim 67 wherein the act of attaching a plurality of electrodes to the patient includes the act of attaching an electrode to a grounding point on the patient's body.

74. The method of claim 67 wherein the act of generating a twelve-lead electrocardiogram includes generating a twelve-lead electrocardiogram in real-time as the electrical signals are acquired.

75. The method of claim 67 wherein the act of acquiring the electrical signals further comprises the act of acquiring the electrical signals with a signal processor coupled to a telemetry monitor.

76. The method of claim 75 wherein the act of acquiring the electrical signals from the electrodes further comprises the act of acquiring electrical signals from the electrodes of more than one patient.

77. The method of claim 67 wherein the act of generating a twelve-lead electrocardiogram further comprises the act of generating leads I, II, III, aVR, aVL, aVF, V1, V2, V3, V4, V5, and V6.

78. The method of claim 77 wherein leads I, II, III, aVR, aVL, aVF, V1 or V2, and V5 generated from the electrical signals are the same as leads I, II, III, aVR, aVL, aVF, V1 or V2, and V5 that would be generated from the electrical signals of a standard ten-electrode, twelve-lead electrocardiograph.

79. The method of claim 78 wherein the act of generating a twelve-lead electrocardiogram further comprises the act of mathematically generating leads V1 or V2, V3, V4, and V6 from the electrical signals.

80. The method of claim 79 wherein the act of generating the leads further comprises the act of using expansion coefficients in the multiple-linear regression.

81. The method of claim 80 wherein the act of generating the leads further comprises the act of determining the expansion coefficients from a data set of electrocardiograms from a general population.

82. The method of claim 80 wherein the act of generating the leads further comprises the act of determining the expansion coefficients from a data set of electrocardiograms from a sub-population based on at least one of sex, age, race, height, weight, and body habitus.

83. The method of claim 80 wherein the act of generating the leads further comprises the act of determining the expansion coefficients from a data set of electrocardiograms from the same patient.

84. A method of generating a twelve-lead electrocardiogram from electrical data acquired from a patient's heart, the method comprising the acts of:
attaching a plurality of less than ten electrodes to the patient, the act of attaching including attaching at least two of the electrodes to the patient's chest in two of the standard ten-electrode, twelve-lead electrocardiogram positions and attaching at least three of the electrodes to the patient's limbs in three of the standard ten-electrode, twelve-lead electrocardiogram positions;
acquiring a first and second channel of data from the electrodes attached to the patient's chest;
acquiring a third and fourth channel of data from the electrodes attached to the patient's limbs;
generating a twelve-lead electrocardiogram from the acquired channels of data.

85. The method of claim 84 wherein the act of attaching electrodes to the patient's chest further comprises the act of attaching an electrode in one of (a) approximately the fourth intercostal space at the right border of the patient's sternum and (b) approximately the fourth intercostal space at the left border of the patient's sternum.

86. The method of claim 84 wherein the act of attaching electrodes to the patient's chest further comprises the act of attaching an electrode in approximately the fifth intercostal space at the patient's anterior axillary line.

87. The method of claim 84 wherein the act of attaching electrodes to the patient's limbs further comprises the act of attaching an electrode to the patient's left arm.

88. The method of claim 84 wherein the act of attaching electrodes to the patient's limbs further comprises the act of attaching an electrode to the patient's right arm.

89. The method of claim 84 wherein the act of attaching electrodes to the patient's limbs further comprises the act of attaching an electrode to the patient's left leg.

90. The method of claim 84 wherein the act of attaching a plurality of electrodes further comprises the act of attaching an electrode to a grounding point on the patient's body.

91. The method of claim 84 and further comprising the act of coupling four amplifiers to the electrodes.

92. The method of claim 91 and further comprising the act of coupling a signal processor to the amplifiers.

93. The method of claim 92 and further comprising the act of coupling the signal processor to a telemetry monitor.

94. The method of claim 93 wherein the act of acquiring the channels of data further comprises the act of acquiring channels of data from more than one patient.

95. The method of claim 84 wherein the act of generating a twelve-lead electrocardiogram further comprises the act of generating leads I, II, III, aVR, aVL, aVF, V1, V2, V3, V4, V5, and V6.

96. The method of claim 95 wherein leads I, II, III, aVR, aVL, aVF, V1 or V2, and V5 generated from the electrical signals are the same as leads I, II, III, aVR, aVL, aVF, V1 or V2, and V5 that would be generated from the electrical signals of a standard ten-electrode, twelve-lead electrocardiogram.

97. The method of claim 96 wherein the act of generating a twelve-lead electrocardiogram further comprises the act of mathematically generating leads V1 or V2, V3, V4, and V6 from the electrical signals.

98. The method of claim 97 wherein the act of generating the leads further comprises the act of generating the leads using multiple-linear regression.

99. The method of claim 98 wherein the act of generating the leads further comprises the act of using expansion coefficients in the multiple-linear regression.

100. The method of claim 99 wherein the act of generating the leads further comprises the act of determining the expansion coefficients from a data set of electrocardiograms from a general population.

101. The method of claim 99 wherein the act of generating the leads further comprises the act of determining the expansion coefficients from a data set of electrocardiograms from a sub-population based on at least one of sex, age, race, height, weight, and body habitus.

102. The method of claim 99 wherein the act of generating the leads further comprises the act of determining the expansion coefficients from a data set of electrocardiograms from the same patient.

103. An electrocardiograph device for acquiring and processing electrical data from a patient's heart, the device comprising:
a plurality of less than ten electrodes attachable to the patient, at least two of the plurality of electrodes attachable to the patient's chest in two of the standard ten-electrode, twelve-lead electrocardiograph positions, the output of the electrodes attachable to the patient's chest being a first and second channel of data, and at least three of the plurality of electrodes attachable to the patient's limbs in three of the standard ten-electrode, twelve-lead electrocardiograph positions, the output of the electrodes attachable to the patient's limbs being a third and fourth channel of data; and a signal processor for acquiring the channels of data and for generating a twelve-lead electrocardiogram from the acquired channels of data.

104. The device of claim 103 wherein the electrodes attachable to the patient's chest include an electrode attachable in one of (a) approximately the fourth intercostal space at the right border of the patient's sternum and (b) approximately the fourth intercostal space at the left border of the patient's sternum.

105. The device of claim 103 wherein the electrodes attachable to the patient's chest include an electrode attachable in approximately the fifth intercostal space at the patient's anterior axillary line.

106. The device of claim 103 wherein the electrodes attachable to the patient's limbs include an electrode attachable to the patient's left arm.

107. The device of claim 103 wherein the electrodes attachable to the patient's limbs include an electrode attachable to the patient's right arm.

108. The device of claim 103 wherein the electrodes attachable to the patient's limbs include an electrode attachable to the patient's left leg.

109. The device of claim 103 wherein the plurality of electrodes include an electrode attachable to a grounding point on the patient's body.

110. The device of claim 103 and further comprising four amplifiers coupled to the electrodes.

111. The device of claim 103 and further comprising a telemetry monitor coupled to the electrodes and to the signal processor.

112. The device of claim 111 wherein the device acquires channels of data from more than one patient.

113. The device of claim 103 wherein the generated twelve-lead electrocardiogram includes leads I, II, III, aVR, aVL, aVF, V1, V2, V3, V4, V5, and V6.

114. The device of claim 113 wherein leads I, II, III, aVR, aVL, aVF, V1 or V2, and V5 generated from the electrical signals are the same as leads I, II, III, aVR, aVL, aVF, V1 or V2, and V5 that would be generated from the electrical signals of a standard ten-electrode, twelve-lead electrocardiogram.

115. The device of claim 113 wherein the signal processor includes a software module for mathematically generating leads V1 or V2, V3, V4, and V6 from the electrical signals.

116. The device of claim 115 wherein the software module generates the leads mathematically from the electrical signals acquired by the signal processor using multiple-linear regression.

117. The device of claim 116 wherein the software module expansion coefficients in the multiple-linear-regression to generate the leads.

118. The device of claim 117 wherein the expansion coefficients are determined from a data set of electrocardiograms from a general population.

119. The device of claim 117 wherein the expansion coefficients are determined from a data set of electrocardiograms from a sub-population based on at least one of sex, age, race, height, weight, and body habitus.

120. The device of claim 117 wherein the expansion coefficients are determined from a data set of electrocardiograms from the same patient.

* * * * *